United States Patent [19]

Davenport

[11] Patent Number: 5,157,142

[45] Date of Patent: Oct. 20, 1992

[54] THIOCARBAMATES AND THEIR DERIVATIVES

[75] Inventor: Kenneth G. Davenport, Corpus Christi, Tex.

[73] Assignee: Hoechst Celanese Corporation, Somerville, N.J.

[21] Appl. No.: 875,158

[22] Filed: Jun. 17, 1986

[51] Int. Cl.$^5$ ............................................ C07C 333/00
[52] U.S. Cl. .................................................. 558/234
[58] Field of Search ................ 558/240, 234; 564/218, 564/393

[56] References Cited

U.S. PATENT DOCUMENTS 3,476,791  11/1969  Newman et al. ..................... 558/240
4,524,217   6/1985  Davenport et al. ................. 558/240

OTHER PUBLICATIONS

Chem. Ber., vol. 58, 1925, pp. 36–51.
Synthetic Communications, 13(11), 941–944(1983).
Pearson et al., J. Am. Chem. Soc., Dec. 1953, pp. 5905–5908.
Newman et al., J. Org. Chemistry, vol. 31, pp. 3980–3984 (1966).
Kwart et al., J. Org. Chemistry, vol. 31, pp. 410–413 (1966).
Reid, Organic Chemistry of Bivalent Sulfur, vol. IV, p. 201, 1962, Chemical Publishing Co. Inc., NY.

*Primary Examiner*—Mary C. Lee
*Assistant Examiner*—Robert C. Whittenbaugh
*Attorney, Agent, or Firm*—Marvin Turken; Donald R. Cassady

[57] ABSTRACT

A process is provided for preparing N-acyl-aminothiophenols, e.g., N-acetyl-para-aminothiophenol, or aminothiophenols, e.g., para-aminothiophenol, by reacting a hydroxy aromatic ketone, e.g., 4-hydroxyacetophenone (4-HAP), with hydroxylamine or a hydroxylamine salt, to form the oxime of the ketone, subjecting the oxime to a Beckmann rearrangement in the presence of a catalyst to form the N-acyl-hydroxy aromatic amine, e.g., N-acetyl-para-aminophenol (APAP), reacting the N-acyl-hydroxy aromatic amine with an N,N-di (organo) thiocarbamoyl halide, e.g., N,N-dimethylthiocarbamoyl chloride, to form an O-(N-acyl-aminoaryl)-N,N-di (organo) thiocarbamate, e.g., O-(N-acetyl-para-aminophenyl)-N,N-dimethylthiocarbamate, pyrolytically rearranging the O-(N-acyl-aminoaryl)-N,N-di (organo) thiocarbamate to form an S-(N-acyl-aminoaryl)-N,N-di (organo) thiocarbamate, e.g., S-(N-acetyl-para-aminophenyl)-N,N-dimethylthiocarbamate, and hydrolyzing the latter compound to obtain the N-acyl aminothiophenol or aminothiophenol. The N-acyl aminothiophenol may be reacted with an acylating agent to form the N,S-diacyl-aminothiophenol, e.g., N,S-diacetyl-p-aminothiophenol, or may be further hydrolyzed to the aminothiophenol, e.g., p-aminothiophenol.

1 Claim, No Drawings

THIOCARBAMATES AND THEIR DERIVATIVES

This invention relates to the production of aminothiophenols, e.g, para-aminothiophenol, and their derivatives, such as N-acyl-aminothiophenols, e.g., N-acetyl-para-aminothiophenol, from hydroxy aromatic ketones, e.g., 4-hydroxyacetophenone.

BACKGROUND OF THE INVENTION

Aminothiophenols and their derivatives have various actual and potential uses in commerce. For example, aminothiophenols such as para-aminothiophenol are important intermediates for the synthesis of pharmaceuticals such as antiarthritics, steroid derivatives, and anti-malarials, and are also used as photograph antifogging agents.

U. S. Pat. No. 4,524,217, issued Jun. 18, 1985 to K. G. Davenport and C. B. Hilton, and assigned to the same assignee as this application, teaches the preparation of N-acyl-hydroxy aromatic amines, e.g., N-acetyl-para-aminophenol (APAP), by reacting a hydroxy aromatic ketone, e.g., 4-hydroxyacetophenone (4-HAP), with hydroxylamine or a hydroxylamine salt, to form the oxime of the ketone, and subjecting the oxime to a Beckmann rearrangement in the presence of a catalyst to form the N-acyl-hydroxy aromatic amine. The patent also discloses the preparation of hydroxy aromatic ketones by the Fries rearrangement of aromatic esters such as phenyl acetate or the Friedel-Crafts acylation of phenols using hydrogen fluoride as catalyst and cites several references disclosing these reactions. The entire disclosure of this patent is incorporated by reference.

Auwers et al, Chemische Berichte 58, 36-51 (1925) show the Beckmann rearrangement of a large number of oximes of aromatic ketones, most of which are substituted acetophenones. However, the only attempted rearrangement of the oxime of a hydroxy aromatic ketone was that of the oxime of o-hydroxyacetophenone, but no amine was formed, i.e., the attempted rearrangement was unsuccessful; see page 41.

Ganboa et al, Synthetic Communications 13, 941-944 (1983) show the production of acetanilide from acetophenone by refluxing in a solution of hydroxylamine hydrochloride. There is, however, no suggestion of the synthesis of N-acyl hydroxy aromatic amines such as N-acetyl-para-aminophenol (APAP).

Pearson et al, Journal of the American Chemical Society 75, 5905-5908 (1953) disclose the formation of hydrazones from ketones by reaction with hydrazine hydrate and the rearrangement of the hydrazone to the amide by reaction with sodium nitrite and concentrated sulfuric acid. Specifically, on page 5907 Pearson et al show the rearrangement of p-hydroxyacetophenone hydrazone to p-hydroxyacetanilide, i.e., APAP.

Newman et al, Journal of Organic Chemistry 31, 3980-3984 (1966), teach the formation of O-aryl dialkylthiocarbamates by reaction of a phenol with a dialkyl thiocarbamoyl chloride, and the pyrolytic rearrangement of O-aryl dialkylthiocarbamates to S-aryl dialkylthiocarbamates. Specifically disclosed in Table I is the pyrolytic rearrangement of O-4-acetamido-to S-4-acetamidodimethylthiocarbamate.

Newman et al, U.S. Pat. No. 3,476,791, disclose a process similar to that disclosed in the article cited in the preceding paragraph and was issued to patentees who are the same as the authors of such article. Example 12 of the patent shows the preparation of p-acetamidophenyl dimethylthiolcarbamate from p-acetamidophenyl dimethylthioncarbamate.

Kwart et al, Journal of Organic Chemistry, 31, 410-413 (1966), show the vapor phase pyrolytic rearrangement of various diaryl thioncarbonates to O,S-diaryl thiolcarbonates and of various O-aryl dialkylthioncarbamates to S-aryl dialkylthiolcarbamates.

SUMMARY OF THE INVENTION

In accordance with this invention, aminothiophenols, e.g., para-aminothiophenol, and their derivatives such as N-acyl-aminothiophenols, e.g., N-acetyl-para-aminothiophenol, are produced by reacting a hydroxy aromatic ketone, e.g., 4-hydroxyacetophenone (4-HAP), with a hydroxylamine or hydroxylamine salt, to form the oxime of the ketone, subjecting the oxime to a Beckmann rearrangement in the presence of a catalyst to form the N-acyl-hydroxy aromatic amine, e.g., N-acetyl-para-aminophenol (APAP), reacting the N-acyl-hydroxy aromatic amine with an N,N-di(organo) thiocarbamoyl halide, e.g., N,N-dimethylthiocarbamoyl chloride (DMTC) to form an O-(N-acyl-aminoaryl)-N,N-di(organo)thiocarbamate, e.g., O-(N-acetyl-para-aminophenyl)-N,N-dimethylthiocarbamate, pyrolytically rearranging the O-(N-acyl-aminoaryl)-N,N-di(organo)thiocarbamate to form an S-(N-acyl-aminoaryl)-N,N-di(organo)thiocarbamate, e.g., S-(N-acetyl-para-aminophenyl)-N,N-dimethylthiocarbamate, and hydrolyzing the S-(N-acyl-aminoaryl)-N,N-di(organo)thiocarbamate to obtain an N-acyl aminothiophenol, e.g., N-acetyl-para-aminothiophenol, or an aminothiophenol, e.g., para-aminothiophenol. The N-acyl-aminothiophenol may be reacted with an acylating agent to form the N,S-diacyl-aminothiophenol, e.g., N,S-diacetyl-4-aminothiophenol, or may be hydrolyzed to the aminothiophenol, e.g., p-aminothiophenol.

Preferably, the hydroxy aromatic ketone, e.g., 4-HAP, is prepared by the Fries rearrangement of an aromatic ester, e.g., phenyl acetate, or the Friedel-Crafts acylation of a phenolic compound, e.g., phenol, with an acylating agent, e.g., acetic acid or acetic anhydride, using hydrogen fluoride as catalyst, since this allows for the production of the N-acyl-aminothiophenol starting with relatively cheap and available raw materials. Conditions for these reactions are shown in the previously cited U.S. Pat. No. 4,524,217, the disclosure of which has been incorporated herein by reference. If 4-HAP is used as an intermediate in obtaining the desired product, the procedures for producing 4-HAP from phenol and acetic acid or anhydride may be used which are disclosed in pending U.S. patent applications, Ser. Nos. 06/714,407, filed Mar. 21, 1985, 06/716,016, filed Mar. 26, 1985, and 06/721,007, filed Apr. 8, 1985, the entire disclosures of which are incorporated by reference. Similarly, if 6-hydroxy-2-acetonaphthone (6,2-HAN) is used as an intermediate, procedures for producing this product by the Friedel-Crafts acylation of 2-naphthol with acetic anhydride or acetic acid, and by the Fries rearrangement of 2-naphthyl acetate are shown respectively in U.S. Pat. No. 4,593,125, issued Jun. 3, 1986 to Davenport et al, and pending application Ser. No. 870062 filed Jun. 3, 1986 by Davenport. The entire disclosures of the foregoing patent and application are incorporated by reference.

The reaction of the hydroxy aromatic ketone with hydroxylamine added as is or from a hydroxylamine salt to form the oxime of the ketone proceeds as shown in equation (I):

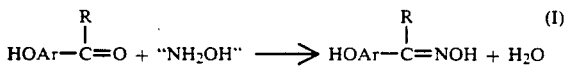

where Ar and R are as defined hereinafter.

The Beckmann rearrangement of the oxime to form an N-acyl-hydroxy aromatic amine proceeds as in equation (II):

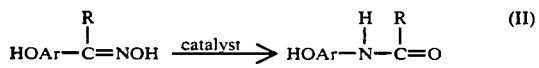

The reaction between the N-acyl-hydroxy aromatic amine with an N,N-di(organo) thiocarbamoyl halide to form an O-(N-acyl-aminoaryl)-N,N-di(organo) thiocarbamate is as shown in equation (III):

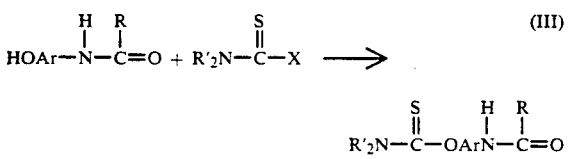

where X is halide, e.g., chloride, or bromide, and R' is a monovalent organo radical as defined hereinafter.

The pyrolytic rearrangement of the O-(N-acyl-aminoaryl)-N,N-di(organo)thiocarbamate to the S-(N-acyl-aminoaryl)-N,N-di(organo)thiocarbamate proceeds as in equation (IV):

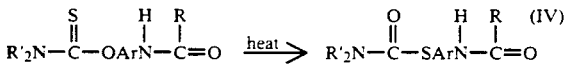

The hydrolysis of the S-(N-acyl-aminoaryl)-N,N-di(organo)thiocarbamate to form the N-acyl aminothiophenol proceeds as in equation (V):

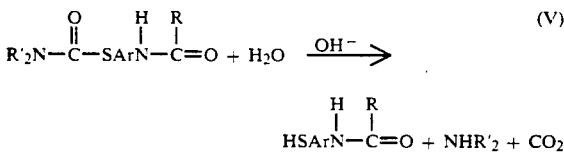

Under more stringent hydrolysis conditions, the hydrolysis results in the formation of the free aminothiophenol as shown in equation (VI):

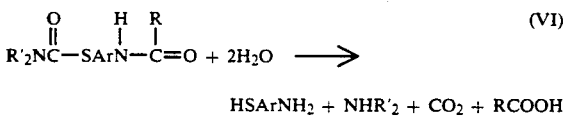

The acylation of the N-acyl aminothiophenol proceeds as in equation (VII):

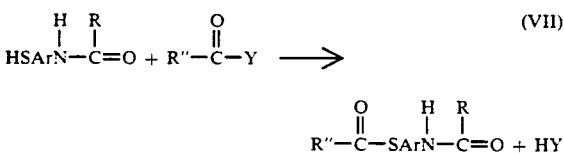

where Y is the residue of an acylating agent as more fully defined hereinafter.

The N-acyl aminothiophenol produced by hydrolysis as in equation (V) may be further hydrolyzed to the aminothiophenol as shown in equation (VIII):

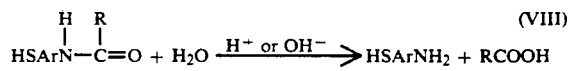

In the foregoing equations Ar is a divalent aromatic radical. The specific nature of the radical is not critical but it is preferably a radical resulting from the removal of two ring hydrogen atoms from benzene or naphthalene, either unsubstituted or with ring hydrogens substituted with radicals such as alkyl, alkenyl, alkynyl, alkoxy or acyloxy containing 1 to 18 carbon atoms, aralkyl containing 7 to 18 carbon atoms; halogen, e.g. chlorine, bromine, or iodine; hydroxy; amino; or sulfhydryl. Ar is preferably 1,4-phenylene or 2,6-naphthylene, with the ketocarbon and corresponding groups occupying the first stated numbered position of Ar when the position are not equivalent. Most preferably Ar is 1,4-phenylene.

R and R'' in the foregoing equations may be the same or different and are each a radical containing, for example, 1 to 18 carbon atoms preferably 1 to 4 carbon atoms. R and R'' may be, for example, alkyl, alkenyl, alkynyl, alkoxyalkyl acylalkyl, or acyloxyalkyl containing 1 to 18 carbon atoms, either unsubstituted or substituted with radicals such as halogen, e.g., chlorine, bromine, or iodine; hydroxy; amino; sulfhydryl; or an aryl radical, which may be a monovalent radical corresponding to the definition of Ar given above except that the carbon bonded to OH is bonded to a hydrogen instead. More preferably, R and R'' are each methyl, ethyl, propyl, or n-butyl and most preferably methyl.

The amine organo groups of the contemplated thiocarbamates, i.e., R' in equations (III), (IV), and (V), are such that the amine nitrogen atom is attached to two different carbon atoms each of which is saturated with hydrogen atoms, other carbon atoms or a combination of those, or is an aromatic ring carbon atom. The organo groups may be, for example, any of the groups identified by Newman et al, as satisfying $R_4$ and $R_5$ in Formula V shown in their U.S. Pat. No. 3,476,791, the entire disclosure of which is incorporated by reference, or such organo groups may be any of those identified previously as satisfying R and R'' in equations (I) to (VII) herein. Preferably, R' is lower alkyl, e.g., containing 1 to 4 carbon atoms such as methyl, ethyl, propyl, or n-butyl and is most preferably methyl.

In equation (VII), Y is the residue minus the acyl group,

of compounds which are known acylating agents, such as hydroxy, acyloxy, e.g., acetoxy, and halide, e.g., fluoride, chloride, and bromide. Acylating agents which may be used are for example alkanoic acids, e.g., acetic and propionic acids, alkanoic acid anhydrides, e.g., acetic and propionic anhydrides, and acyl halides, e.g., acetyl and propionyl fluorides, chlorides, and bromides.

Preferably, the process of the invention is carried out such that, in the foregoing equations, Ar is 1,4-phenylene, R, R' and R" are methyl, and X and Y are chloride, such that 4-hydroxyacetophenone (4-HAP) is reacted with hydroxylamine or a hydroxylamine salt, to form the 4-HAP oxime (equation I), the latter is subjected to a Beckmann rearrangement to form N-acetyl-para-aminophenol (APAP), (equation II), the APAP is reacted with N,N-dimethylthiocarbamoyl chloride (DMTC) to form O-(N-acetyl-p-aminophenyl)-N,N-dimethyl thiocarbamate (equation III), which in turn is pyrolytically rearranged to form S-(N-acetyl-p-aminophenyl)-N,N-dimethylthiocarbamate (equation IV), which is hydrolyzed to N-acetyl-para-aminothiophenol (equation V), or p-aminothiophenol (equation VI). The former compound may then be acetylated, e.g., with acetic anhydride, to form N,S-diacetyl-p-aminothiophenol (equation VI), or may be further hydrolyzed to form para-aminothiophenol (equation VIII).

The conversion of hydroxy aromatic ketones, e.g., 4-HAP, into N-acyl-hydroxy aromatic amines, e.g., APAP, is accomplished by first forming the oxime of the hydroxy aromatic ketone as indicated by equation (I), by contacting the ketone with hydroxylamine or a hydroxylamine salt, e.g., hydroxylamine hydrochloride, hydroxylamine sulfate, hydroxylamine bisulfate, or hydroxylamine phosphate, and a base if a hydroxylamine salt is employed, e.g., ammonium hydroxide, potassium hydroxide, sodium hydroxide, or lithium hydroxide in an amount, for example, of 1 to 3 moles per mole of hydroxylamine salt, at a temperature, for example of 0 to 60° C. for a period, for example, of 1 to 4 hours. Any pressure may be used, e.g., 80 mm of mercury to 10 atmospheres absolute. The reaction is preferably carried out in an aqueous or alcoholic medium, i.e., in the presence of water and/or an alcohol such as methanol, ethanol, or isopropanol.

The oxime is converted into the corresponding N-acyl-hydroxy aromatic amine by a Beckmann rearrangement as shown in equation (II), by contacting the oxime with a catalyst for the reaction at a temperature, for example, of 0 to 118° C. for a period of 1 to 4 hours. The pressure is not critical and may be, for example, in the range of 80 mm of mercury to 10 atmospheres absolute. Any Beckmann rearrangement catalyst may be used, as for example, an acid, e.g., a mineral acid such as sulfuric or hydrochloric acid, an organic acid such as trifluoroacetic acid, para-toluenesulfonic acid, benzenesulfonic acid or methanesulfonic acid, an acidic ion-exchange resin such as Amberlyst 15 or Nafion 501 which are sulfonic acid ion-exchange resins, or thionyl chloride in liquid sulfur dioxide. The reaction may be advantageously carried out in the presence of the glacial carboxylic acid corresponding to the N-acyl group of the desired reaction product. The total amount of glacial carboxylic acid is not critical but is usually present such that the oxime concentration is in the range of 2 to 50% by weight at the start of the reaction.

The formation of O-(N-acyl-aminoaryl)-N,N-di(organo) thiocarbamate indicated by equation (III) is accomplished by contacting the N-acyl-hydroxy aromatic amine, e.g., APAP, with the N,N-di(organo) thiocarbamoyl halide, e.g., DMTC, at a temperature of about 25° to 50° C. for a period of about 30 to 60 minutes. Preferably the reaction is carried out in the presence of a base, e.g., sodium hydroxide, potassium hydroxide, sodium hydride, or sodium methoxide. The reaction may be carried out in the presence of an appropriate solvent, e.g., one which is capable of dissolving at least part of the reactants and is inert to the reaction. Solvents which can be used are sulfolane, dimethyl formamide, and alcohols, e.g., methanol, ethanol and t-butanol.

The pyrolytic rearrangement of the foregoing O-aryl thiocarbamate to the S-(N-acyl-aminoaryl)-N,N-di(organo) thiocarbamate, for example, is accomplished by heating the O-aryl compound to a temperature of about 200° to 300° C. for a period of about 30 to 120 minutes. In general, the lower the temperature, the longer the period of time to effect substantially complete rearrangement of the O-aryl to the S-aryl thiocarbamate.

The hydrolysis of the S-arylthiocarbamate shown in equations (V) and (VI) may be accomplished by heating the compound and a base, e.g., sodium or potassium hydroxide or an alkyl amine, in an aqueous glycol or alcohol, e.g., methanol, ethanol, or t-butanol solution in an inert atmosphere, e.g., of nitrogen, under reflux conditions. For example, to obtain an N-acyl aminothiophenol as shown in equation (V) a solution of about 0.5 to 2 M concentration of S-aryl thiocarbamate and about 1 to 4 M concentration of a base such as potassium or sodium hydroxide in aqueous ethylene glycol, or alcohol, e.g., containing about 25 to 50 wt. % of water, may be refluxed for about 1 to 4 hours. To obtain the free aminothiophenol as shown in equation (VI), a solution of S-aryl thiocarbamate, e.g., about 2 to 8 M concentration in the same base solution may be refluxed for a longer period, e.g., about 4 to 8 hours.

The acylation of the N-acyl aminothiophenol to obtain the N,S-diacylaminothiophenol as shown in equation (VI) may be carried out, for example, by contacting the former compound with about 1 to 10 moles of an acylation agent such as acetic anhydride, per mole of N-acyl aminothiophenol at a temperature of about 20° to 140° C. for a period of about 15 to 120 minutes either in the absence or presence of base, e.g., potassium hydroxide or sodium acetate.

DESCRIPTION OF SPECIFIC EMBODIMENTS

The following examples further illustrate the invention.

Examples 1 to 3 illustrate the formation of 4-hydroxyacetophenone oxime from 4-hydroxyacetophenone and a hydroxylamine salt, as shown in equation (I), wherein Ar is 1,4-phenylene and R is methyl.

EXAMPLE 1

A solution was prepared by adding 13.6 g (0.1 mol) of 4-hydroxyacetophenone, 7.6 g (0.11 mol) of hydroxylamine hydrochloride, and 10 g of water to 40 mL of ethanol. To the solution was added 5.0 g of 30% ammonium hydroxide which was then heated at reflux for 2 h. The ethanol was removed on a rotary evaporator to yield a yellow oil. An extractive work-up afforded 15.1 g (99%) of 4-hydroxyacetophenone oxime.

EXAMPLE 2

A solution was prepared by adding 20.4 g (0.15 mol) of 4-hydroxyacetophenone and 13.0 g (0.08 mol) of hydroxylamine sulfate to 100 mL of water at 70° C. To the solution was added 16.3 mL of 30% ammonium hydroxide which was then heated at reflux for 0.5 h. White crystals formed upon cooling yielding 21.0 g (92.6%) of 4-hydroxyacetophenone oxime.

EXAMPLE 3

A solution was prepared by adding 20.4 g (0.15 mol) of 4-hydroxyacetophenone and 12.9 g (65.6 mmol) of hydroxylamine phosphate to 100 mL of water at 70° C. To the solution was added 16.3 mL of 30% ammonium hydroxide which was then heated at reflux for 0.5 h. White crystals formed upon cooling yielding 21.0 g (92.6%) of 4-hydroxyacetophenone oxime.

Examples 4, 5, and 6 illustrate the formation of N-acetyl-para-aminophenol (APAP) by the Beckmann rearrangement of 4-hydroxyacetophenone oxime using an acid catalyst as shown in equation (II) wherein Ar is 1,4-phenylene and R is methyl.

EXAMPLE 4

A mixture of 3.0 g of Amberlyst 15, (a sulfonic acid ion-exchange resin made by Rohm & Haas), 3.0 g (22.0 mmol) of 4-hydroxyacetophenone oxime, and 50 mL of acetic acid was heated at reflux under nitrogen for 2 h. The ion exchange resin was then removed and the acetic acid was distilled in vacuo to afford an orange residue. The residue was dissolved in ethanol and treated with activated carbon and anhydrous magnesium sulfate. The mixture was filtered to produce a clear, yellow filtrate. Removal of the ethanol using a rotary evaporator produced 2.9 g of a yellow oil, which upon drying afforded 2.0 g (66.7%) of N-acetyl-para-aminophenol.

EXAMPLE 5

A solution of 10 g (66.2 mmol) of 4-hydroxyacetophenone oxime and 75 g of trifluoroacetic acid was heated at reflux under a nitrogen atmosphere. The trifluoroacetic acid was then removed in a rotary evaporator to afford 14.7 g of oil which was dissolved in 100 mL of water. Upon cooling to 0° C. for 0.5 h, crystallization occurred. Filtration and drying of the crystals yielded 7.1 g (71%) of N-acetyl-para-aminophenol.

EXAMPLE 6

A pressure bottle (cooled in a $CO_2$/acetone bath) was charged with 50 mL of $SO_2$, 0.05 mL of $SOCl_2$, and 15 g (0.1 mol) of 4-hydroxyacetophenone oxime. The $CO_2$/acetone bath was removed and the contents of the pressure bottle stirred for 1.5 h at room temperature. The $SO_2$ was then vented and the crystals were washed from the pressure bottle with 50 mL of warm water. The pH of the aqueous slurry was adjusted to 6.5 by dropwise addition of 30% $NH_4OH$. The slurry was cooled in an ice bath and then filtered. The filtered crystals were washed with 10 mL of ice water and dried overnight in a vacuum oven (60° C./100 mm Hg) yielding 13.3 g (88.7%) of white crystals of N-acetyl-para-aminophenol having a melting point of 166.5–170° C.

Example 7 illustrates the formation of O-(N-acetyl-para-aminophenyl)-N,N-dimethylthiocarbamate by reaction of N-acetyl-para-aminophenol (APAP) with N,N-dimethylthiocarbamoyl chloride (DMTC) in accordance with equation (III) wherein Ar is 1,4-phenylene, R and R' are methyl and X is chloride.

EXAMPLE 7

A base solution was prepared by adding 30.8 g (0.55 mol) of potassium hydroxide and 250 mL of methanol to a 1 liter 3-necked roundbottomed flask equipped with a mechanical stirrer and then cooled in an ice-water bath. To this solution was added 75.5 g (0.5 mol) of N-acetyl-para-aminophenol (APAP). The mixture was stirred for 15 min whereupon 75.8 g (0.5 mol) of N,N-dimethylthiocarbamoyl chloride was added resulting in an exotherm. The mixture was stirred for 0.5 h, cooled in ice-water bath, and poured into 750 mL of cold water. A white solid precipitated which was collected via filtration and washed with water. The product was dried in vacuo (150 mmHgA) at 50° C. to afford 80.1 g (67% yield) of a white solid which was determined to be O-(N-acetyl-para-aminophenyl)-N,N-dimethylthiocarbamate.

Example 8 illustrates the formation of S-(N-acetyl-para-aminophenyl)-N,N-dimethylcarbamate by the pyrolytic rearrangement of O-(N-acetyl-para-aminophenyl)N,N-dimethylthiocarbamate in accordance with equation (IV).

EXAMPLE 8

A mixture of 20.0 g (0.084 mol) of O-(N-acetyl-para-aminophenyl) dimethylthiocarbamate and 50 mL of sulfolane was heated at 280° C. under nitrogen for 2 h. Distillation of the sulfolane under reduced pressure left behind an oily liquid in the flask. Trituration of the oily liquid with 50 mL of water afforded a tan solid. The solid was dissolved in 100 mL of dichloromethane and washed with 100 mL of water (2×). The organic layer was separated, dried over anhydrous magnesium sulfate, and concentrated in vacuo to afford 16.0 g (80% yield) of a tan solid which was determined to be S-(N-acetyl-para-aminophenyl)-N,N-dimethylthiocarbamate.

Example 9 illustrates the formation of N-acetyl-para-aminothiophenol by the hydrolysis of S-(N-acetyl-para-aminophenyl)-N,N-dimethylthiocarbamate as shown in equation (V).

EXAMPLE 9

A base solution was prepared by adding 1.12 g (0.02 mol) of potassium hydroxide to 5 mL of water and 10 mL of ethylene glycol. To the solution was added 2.38 g (0.01 mol) S-(N-acetyl-para-aminophenyl)-N,N-dimethylthiocarbamate. The reaction mixture was heated at reflux for 1.5 h, cooled to room temperature, and extracted with 20 mL of ether. Concentration of the organic layer yielded 0.4 g of solid characterized as unreacted starting material. The aqueous layer was carefully acidified to pH 6.0 and extracted with 50 mL of ether (3×). Concentration of this organic layer afforded a 1.1 g (66%) of solid characterized as N-acetyl-para-aminothiophenol.

Example 10 illustrates the formation of para-aminothiophenol by the hydrolysis of S-(N-acetyl-para-aminophenyl)-N,N-dimethylthiocarbamate in accordance with equation (VI) under more stringent conditions than are shown in Example 9.

EXAMPLE 10

A base solution is prepared by adding 2.24 g (0.04 mol) of potassium hydroxide to 5 mL of water and 10 mL of ethylene glycol. To the solution are added 2.38 g (0.01 mol) S-(N-acetyl-para-aminophenyl)-N,N-dimethylthiocarbamate. The reaction mixture is heated at reflux for 3 h, cooled to room temperature and extracted with 20 mL of water. The aqueous layer is carefully acidified to pH 6.0 and extracted with 50 mL of ether (3×). Concentration of this organic layer affords a yellow solid characterized as para-aminothiophenol.

Example 11 illustrates the formation of para-aminothiophenol by the further hydrolysis of N-acetyl-para-aminothiophenol, as shown in equation (VIII).

EXAMPLE 11

A base solution is prepared by adding 2.24 g (0.04 mol) of potassium hydroxide to 5 mL of water and 10 mL of ethylene glycol. To the solution are added 1.7 g (0.01 mol) of N-acetyl-para-aminothiophenol. The reaction mixture is heated at reflux for 4 h, cooled to room temperature, and extracted with 50 mL of ether. The aqueous layer is carefully acidified to pH 6.0 and extracted with 50 mL of ether (3×). Concentration of this organic layer affords a yellow solid characterized as para-aminothiophenol.

Example 12 illustrates the formation of N,S-diacetyl-para-aminothiophenol by the acylation with acetic anhydride of N-acetyl-para-aminothiophenol, as shown in equation (VII).

EXAMPLE 12

A base solution was prepared by adding 1.68 g (0.03 mol) of potassium hydroxide to 15 mL of methanol. Addition of 4.2 g (0.025 mol) of N-acetyl-para-aminothiophenol was immediately followed by dropwise addition of 3.3 g (0.033 mol) of acetic anhydride. After stirring at room temperature for 15 min, the methanol was removed on a rotary evaporator. The product was precipitated by addition of 50 mL of water, collected by filtration, and washed with water. After drying in vacuo (150 mmHgA) at 50° C. overnight, 4.2 g (80%) of white crystalline product was characterized as N,S-diacetyl-para-aminothiophenol.

Example 13 illustrates the formation of 6-hydroxy-2-acetonaphthone oxime from 6-hydroxy-2-acetonaphthone (6,2,HAN) and hydroxylamine sulfate, as shown in equation (I), wherein Ar is 2,6-naphthylene and R is methyl.

EXAMPLE 13

A solution was prepared by adding 18.6 g (0.1 mol) of 6-hydroxy-2-acetonaphthone, 32.4 g (0.2 mol) of hydroxylamine sulfate, and 90 g of water to 50 mL of ethanol. The mixture was heated at 75° C. for 1 h whereupon 6 mL of 17 M ammonium hydroxide was added. The mixture was then heated at reflux for 1 h. To the reaction mixture was added 200 mL of water. The mixture was cooled and the precipitated solid was collected via filtration. The solid was dried in vacuo (150 mmHgA) at 50° C. to afford 19.5 g (97%) of 6-hydroxy-2-acetonaphthone oxime.

Example 14 illustrates the formation of N-acetyl-6-amino-2-naphthol by the Beckmann rearrangement of 6-hydroxy-2-acetonaphthone oxime using an acid catalyst as shown in equation (II), wherein Ar is 2,6- naphthylene and R is methyl.

EXAMPLE 14

A solution was prepared by dissolving 10.0 g (0.05 mol) of 6-hydroxy-2-acetonaphthone oxime in 50 g of nitromethane. Dropwise addition of 0.2 mL of thionyl chloride to the solution maintained at room temperature under reduced pressure (40 mmHgA) caused an exotherm to occur. The reaction mixture was stirred for an additional 0.5 h upon completion of addition of thionyl chloride. Cooling of the reaction mixture in an ice-water bath caused a solid to precipitate. The solid was collected via filtration and recrystallized from methanol/water. Oven drying of the solid under reduced pressure (150 mmHgA) at 50° C. afforded 6.1 g (61%) of N-acetyl-6-amino-2-naphthol.

Example 15 illustrates the formation of O-(N-acetyl-6-amino-2-naphthyl)N,N-dimethylthiocarbamate by reaction of N-acetyl-6-amino-2-naphthol with N,N-dimethylthiocarbamoyl chloride in accordance with equation (III), wherein Ar is 2,6-naphthylene, R and R' are methyl and X is chloride.

EXAMPLE 15

A base solution was prepared adding 1.3 g (0.024 mol) of potassium hydroxide to 20 mL of methanol. To this solution was added 4.02 g (0.02 mol) of N-acetyl-6-amino-2-naphthol. The mixture was stirred for 15 min whereupon 2.95 g (0.024 mol) of N,N-dimethylthiocarbamoyl chloride was added resulting in an exotherm. The mixture was stirred for 15 min and poured into 200 mL of cold water. A solid precipitated which was collected via filtration and washed with water. The product was dried in vacuo (150 mmHgA) at 50° C. to afford 5.3 g (92%) of a solid characterized by $^1$H NMR and IR as O-(N-acetyl-6-amino-2-naphthyl)N,N-dimethylthiocarbamate.

Example 16 illustrates the formation of S-(N-acetyl-6-amino-2-naphthyl)-N,N-dimethylthiocarbamate by the pyrolytic rearrangement of O-(N-acetyl-6-amino-2-naphthyl)-N,N-dimethylthiocarbamate in accordance with equation (IV).

EXAMPLE 16

A mixture of 2.88 g (0.01 mol) of O-(N-acetyl-6-amino-2-naphthyl)-N,N-dimethylthiocarbamate and 25 mL of sulfolane was heated at 280° C for 2 h under nitrogen. Distillation of the sulfolane under reduced pressure left behind an oily residue in the flask. The residue was extracted with 100 mL of ethyl acetate and the extract was then washed with water. The organic phase was separated from the aqueous phase, dried over anhydrous magnesium sulfate, and filtered. Removal of the ethyl acetate using a rotary evaporator afforded an 1.0 g of an oily solid characterized by $^1$H NMR and IR as S-(N-acetyl-6-amino-2-naphthyl)N-N-dimethylthiocarbamate.

Using the procedures of Examples 9 to 12, S-(N-acetyl-6-amino-2-naphthyl)-N,N-dimethylthiocarbamate may be acylated to N,S-diacetyl-6-amino-2-thionaphthol, or may be hydrolyzed to N-acetyl-6-amino-2-thionaphthol or 6-amino-2-thionaphthol, and N-acetyl-6-amino-2-thionaphthol, may be further hydrolyzed to 6-amino-2-thionaphthol, in accordance with equations (V) to (VIII).

I claim:

1. As a new composition of matter O-(N-acetyl-6-amino-2-naphthyl)-N,N-dimethythiocarbamate.

* * * * *